(12) United States Patent
Karas

(10) Patent No.: US 6,194,602 B1
(45) Date of Patent: Feb. 27, 2001

(54) TERTIARY ALKYL ESTER PREPARATION

(75) Inventor: Lawrence J. Karas, West Chester, PA (US)

(73) Assignee: ARCO Chemical Technology, L.P., Greenville, DE (US)

( * ) Notice: Subject to any disclaimer, the term of this patent is extended or adjusted under 35 U.S.C. 154(b) by 94 days.

(21) Appl. No.: 09/061,678

(22) Filed: Apr. 16, 1998

(51) Int. Cl.$^7$ .................................................. C07C 67/04
(52) U.S. Cl. ............................................ 560/247; 560/241
(58) Field of Search ..................................... 560/247, 241

(56) References Cited

U.S. PATENT DOCUMENTS

| | | | |
|---|---|---|---|
| 2,678,332 | 5/1954 | Cottle et al. | 560/96 |
| 2,882,244 * | 4/1959 | Milton | 252/455 |
| 3,031,495 | 4/1962 | Young et al. | 560/247 |
| 3,037,052 | 5/1962 | Bortnick et al. | 560/193 |
| 3,130,007 * | 4/1964 | Breck | 23/113 |
| 3,172,905 | 3/1965 | Eckert et al. | 560/247 |
| 3,173,943 | 3/1965 | Hess et al. | 502/150 |
| 3,190,939 * | 6/1965 | Benesi | 585/739 |
| 3,308,069 * | 3/1967 | Wadlinger et al. | 252/455 |
| 3,492,341 * | 1/1970 | Trevillyan | 260/497 |
| 3,678,099 | 7/1972 | Kemp | 560/247 R |
| 3,767,568 * | 10/1973 | Chen | 208/134 |
| 4,365,084 | 12/1982 | Young | 560/247 |
| 4,443,379 * | 4/1984 | Taylor et al. | 260/427 |
| 4,461,729 | 7/1984 | Young | 260/459 R |
| 4,465,852 | 8/1984 | Sato | 560/247 |
| 5,866,714 * | 2/1999 | Szady et al. | 560/247 |

OTHER PUBLICATIONS

Pavlov et al., Bull. Soc. Chem. Fr, No. 12, pp. 2985–2986, 1974.*

Pavlov et al, "General Preparative Method for the Esterification of Carboxylic Acids with Isobutylene in the Presence of Tertbutylene", Bull. Soc. Chem. Fr, No. 12, pp. 2985–2986 (1974).

* cited by examiner

*Primary Examiner*—Rosalynd Keys
(74) *Attorney, Agent, or Firm*—William C. Long

(57) ABSTRACT

A tertiary olefin such as isobutylene is reacted with a lower carboxylic acid to produce the ester in the presence of a large pore zeolite catalyst such as Zeolite Y, Zeolite beta or Zeolite X.

8 Claims, No Drawings

TERTIARY ALKYL ESTER PREPARATION

BACKGROUND OF THE INVENTION

1. Field of the Invention

The present invention provides an improved method for the preparation of esters such as t-butyl acetate by reaction of a tertiary olefin with acetic acid in the presence of a large pore zeolite catalyst such as Zeolite Y, Zeolite X or Zeolite beta.

2. Description of the Prior Art

It is known to produce esters by the reaction of an olefin such as isobutylene with a lower carboxylic acid over a sulfonate group-containing cation exchange resin. See U.S. Pat. No. 3,678,099 and the references disclosed therein including U.S. Pat. Nos. 2,678,332, 3,031,495, 3,172,905 and 3,173,943.

A problem which is encountered in such prior procedures has been the tendency for polymerization of the olefin to occur during the esterification which results both in significant yield losses and in the formation of products such as olefin dimer which are difficult to separate from the product ester. For example, isobutylene dimer forms an azeotrope with t-butyl acetate thus making separation exceedingly difficult.

Problems of diisobutylene formation can be substantially overcome through the use of a selectivity enhancing modifier such as tertiary butanol. However, although the use of such a modifier has striking advantages, its use entails additional processing costs and purification procedures.

Other processes are described. For example, U.S. Pat. No. 3,492,341 describes the reaction of isobutylene with acetic acid to form ester using a mordenite aluminosilicate catalyst.

U.S. Pat. No. 4,365,084 describes ester production by reaction of a linear or slightly branched olefin with acetic acid using a catalyst such as HZSM-5. The use of olefins having unsaturation at the number 2 carbon atom is excluded.

U.S. Pat. No. 4,461,729 is similar to 4,365,084 and contains the additional step of hydrolyzing the ester to form secondary alcohol.

U.S. Pat. No. 4,465,852 relates to ester preparation by reaction of olefin with acetic acid. Although a great number of olefins are mentioned, including isobutylene, and a great number of catalysts are mentioned, including ZSM-5, the olefins exemplified are ethylene and propylene and the claims are limited to ethylene, propylene and butylene.

Copending patent application Ser. No. 09/022183, now U.S. Pat. No. 5,994,578 filed Feb. 11, 1998 describes ester preparation by reaction of an olefin such as isobutylene with acetic acid using a ZSM-5 catalyst. Data are presented indicating that at the reported conditions of the testing, poor results were achieved with large pore zeolite catalyst, Zeolite beta.

BRIEF DESCRIPTION OF THE INVENTION

In accordance with the invention, olefin and lower carboxylic acid are reacted in the presence of a large pore acidic zeolite such as Zeolite Y, Zeolite X, or Zeolite beta at conditions where ester is formed at high rates and selectivity, and whereby the formation of olefin polymerization products is maintained at a very low level.

DETAILED DESCRIPTION

The present invention is applicable to the formation of esters having the formula

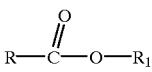

wherein $R_1$ is a $C_4$ or $C_5$ tertiary alkyl group and R is hydrogen or a $C_1$–$C_2$ alkyl group. T-butyl acetate is an especially preferred product.

In accordance with the invention, olefin and organic carboxylic acid are reacted in the liquid phase to form ester over a solid acidic large pore size zeolite catalyst. The large pore zeolites used in accordance with the invention are those having twelve-ring pores as described, for example, at page 19 of "Introduction to Zeolite Science and Practice", van Bekkum et al. Elsevier (1991). Zeolite Y is especially useful as is Zeolite beta and Zeolite X. The zeolites employed are suitably made with conventional binders, eg. alumina, silica, and the like.

The conditions at which the esterification reaction is carried out are exceedingly important. The large pore acidic zeolites are extremely active catalysts and unless certain reaction conditions are employed, excessive amounts of olefin polymer are obtained.

The esterification reaction is carried out at pressures sufficient to maintain the liquid phase, usually 50 psig or higher. The upper pressure limit is governed largely by practical considerations, little is to be gained by operating at pressures in excess of 800 psig. Operation at 250–500 psig is generally preferred.

Reaction temperature is important, temperatures of about 20 to 80° C. are suitable, temperatures of about 35 to 50° C. are preferred.

Excessive contact times, especially at the higher temperature ranges are to be avoided. Reactant liquid weight hourly space velocities (WHSV) of about 10–100 $hr^{-1}$, preferably 25 to 50 $hr^{-1}$ are employed. These figures are based on the large pore zeolite content of the catalyst contact solid.

The mol ratio of olefin to carboxylic acid can vary widely, ratios of 0.1–10 mols olefin per mol carboxylic acid are generally useful, ratios of 0.125 to 0.5 mols olefin per mol carboxylic acid are especially useful. The higher amounts of acid relative to olefin improve reaction selectivity and further aid in suppressing dimer make.

Where a selectivity enhancing modifying agent such as described in copending application Ser. No. 08/816,704 filed Mar. 13, 1997 is used, reaction conditions outside the above ranges can be used. For example, higher temperatures and longer contact times can be employed as can higher olefin to carboxylic acid ratios where the modifier is used. For example, reaction temperatures in the upper part of the 20–80° C. range can be used and liquid hourly space velocities below 10 $hr^{-1}$, eg. as low as 4 $hr^{-1}$ can be used where a selectivity enhancing modifier is used.

Especially preferred selectivity enhancing modifiers, where one is used, are t-butyl alcohol, t-amyl alcohol and the lower ($C_1$–$C_3$) alkyl ethers thereof such as methyl tertiary butyl ether, methyl tertiary amyl ether, and the like. Where used, at least 1 wt % of modifier based on the feed is used up to about 50 wt %.

The following examples illustrate the invention:

A series of esterification runs were carried out using large pore zeolite catalysts and reacting isobutylene and acetic acid to form t-butyl acetate, the runs were carried out at 500 psig. The following table shows the catalyst employed, the feed reactant composition, and the results obtained:

TABLE 1

| Run | Catalyst | Reaction Temp., °C. | WHSV hr.$^{-1}$ | Molar AcOH: i-C$_4$ | % i-C$_4$ Conversion | % Sel. TBAC | % Sel. DIB | % Sel. TIB | % Sel. OTHERS |
|---|---|---|---|---|---|---|---|---|---|
| 1 | 21.0 g A | 75 | 5.5 | 2.0:1 | 85 | 17.4 | 42.6 | 26.7 | 13.3 |
| 2 | 21.0 g A | 60 | 5.3 | 1.7:1 | 62 | 77.2 | 21.5 | 1.2 | 0.2 |
| 3 | 21.0 g A | 50 | 5.6 | 1.9:1 | 61.6 | 89.6 | 10.0 | 0.3 | 0.1 |
| 4 | 21.0 g A | 40 | 5.6 | 1.8:1 | 56.9 | 93.5 | 6.3 | 0.2 | — |
| 5 | 20.0 g B | 80 | 2.88 | 7.4:1 | 5.8 | 96.3 | 3.7 | — | — |
| 6 | 5.0 g A 15.0 g B | 60 | 11.5 | 8.2:1 | 81.0 | 55.6 | 34.8 | 8.2 | 1.4 |
| 7 | 5.0 g A 15.0 g B | 60 | 23.2 | 8.2:1 | 79.1 | 76.2 | 21.0 | 2.6 | 0.3 |
| 8 | 5.0 g A 15.0 g B | 50 | 23.7 | 8.4:1 | 82.4 | 94.1 | 5.6 | 0.3 | — |
| 9 | 5.0 g A 15.0 g B | 40 | 23.4 | 8.6:1 | 86.2 | 97.8 | 2.1 | 0.1 | — |
| 10 | 5.0 g A 15.0 g B | 40 | 36.0 | 8.2:1 | 73.5 | 97.9 | 2.0 | 0.1 | — |
| 11 | 5.0 g A 15.0 g B | 35 | 23.7 | 8.4:1 | 81.0 | 98.3 | 1.6 | 0.1 | — |
| 12 | 5.0 g A 15.0 g B | 35 | 35.4 | 8.1:1 | 69.6 | 98.4 | 1.6 | — | — |
| 13 | 5.0 g A 15.0 g B | 50 | 35.8 | 8.2:1 | 73.7 | 95.7 | 4.1 | 0.2 | — |
| 14 | 5.0 g A 15.0 g B | 60 | 23.4 | 8.4:1 | 88.4 | 8.8 | 13.9 | 72.5 | 4.7 |
| 15 | 5.0 g A 15.0 g B | 40 | 23.7 | 8.4:1 | 85.1 | 69.7 | 16.1 | 13.5 | 0.7 |
| 16 | 5.0 g A 15.0 g B | 40 | 36.0 | 7.7:1 | 79.6 | 79.2 | 12.9 | 7.5 | 0.4 |
| 17 | 2.5 g C 17.5 g B | 40 | 48.3 | 8.6:1 | 84.7 | 83.4 | 11.3 | 5.0 | 0.3 |
| 18 | 2.5 g C 17.5 g B | 40 | 71.1 | 8.1:1 | 75.9 | 86.1 | 10.1 | 3.5 | 0.2 |
| 19 | 5.0 g C 15.0 g B | 40 | 23.8 | 8.1:1 | 83.6 | 71.6 | 14.4 | 13.2 | 0.8 |
| 20 | 5.0 g C 15.0 g B | 40 | 35.8 | 8.2:1 | 85.0 | 82.1 | 10.9 | 6.6 | 0.4 |
| 21 | 5.0 g C 15.0 g B | 40 | 34.9 | 8.0:1 | 82.9 | 93.5 | 5.5 | 0.9 | 0.1 |
| 22 | 2.5 g C 17.5 g B | 40 | 69.8 | 8.0:1 | 65.1 | 95.3 | 4.6 | 0.1 | — |

In the above tables,
ACOH is acetic acid
i-C$_4$ is isobutylene
TBAC is t-butyl acetate
DIB is diisobutylene
TIB is triisobutylene
Space velocity is based on zeolite content of contact solid
Catalyst A is Zeolite Y
Contact solid B is inert alumina
Catalyst C is Zeolite beta In the above, Run 1 is comparative showing the high production of isobutylene polymers at high temperatures and low space velocity.

In Runs 2–4, 10 wt % tertiary butyl alcohol was added to the feed as a selectivity enhancing modifier. As a result of the use of the modifier, selectivity to the ester was greatly improved at the conditions employed, i.e. low space velocities. The data also show the pronounced effect on selectivity of reduction of the reaction temperature.

Run 5 was carried out without the large pore zeolite, only inert solid alumina was used. Only minimal conversion was achieved.

Runs 6–13 were carried out with a mixture of Zeolite Y and inert alumina as contact solid. The data show the excellent results achieved without modifier, and indicate the beneficial effects of reducing reaction temperature and decreasing contact time on ester production.

Runs 14–22 were carried out using a mixture of Zeolite beta and inert alumina as the contact solid.

Run 14 illustrates the relatively poor results obtained at higher temperatures (60° C.) as compared with operation at lower temperature (40° C.) in Run 15. A comparison of Runs 15 and 16 shows the effect of lowering contact time on ester selectivity.

In Runs 21 and 22, the feed contained 2 wt % tertiary butyl alcohol as selectivity enhancing modifier. A comparison of results obtained in these runs with the results in Run 20 and 18 shows the substantial effect of the modifier on ester selectivity.

What is claimed is:

1. In the reaction of a C$_4$ or C$_5$ olefin with a lower carboxylic acid in the presence of a solid acidic catalyst, the improvement which comprises carrying out the reaction in the presence of a large pore acidic zeolite selected from the group consisting of zeolite beta, zeolite X and zeolite Y at conditions effective for the selective production of ester product.

2. In the reaction of a C$_4$ or C$_5$ olefin with a lower carboxylic acid in the presence of a solid acidic catalyst to form product ester, the improvement which comprises carrying out the reaction in the presence of a large pore acidic zeolite selected from the group consisting of zeolite beta, zeolite X and zeolite Y at the following conditions:
   a) temperature in the range of about 20–80° C.,
   b) WSHV in the range of about 10–100 hr$^{-1}$, c) olefin to acid feed mol ratio of about 0.1–10 mols olefin per mol acid, d) pressure sufficient to maintain the liquid phase.

3. The process of claim 2 wherein the olefin is isobutylene.

4. The process of claim 2 wherein the carboxylic acid is acetic acid.

5. The process of claim 2 wherein the solid acidic catalyst is Zeolite beta.

6. The process of claim 2 wherein the solid acidic catalyst is Zeolite X.

7. The process of claim 2 wherein the solid acidic catalyst is Zeolite y.

8. The process of claim 1 wherein a selectivity enhancing modifier is used.

* * * * *